United States Patent
Pavliv et al.

(10) Patent No.: US 11,806,400 B2
(45) Date of Patent: *Nov. 7, 2023

(54) INJECTABLE IBUPROFEN FORMULATION

(71) Applicant: Cumberland Pharmaceuticals Inc., Nashville, TN (US)

(72) Inventors: Leo Pavliv, Cary, NC (US); Andrew Vila, Nashville, TN (US)

(73) Assignee: Cumberland Pharmaceuticals Inc., Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/869,277

(22) Filed: May 7, 2020

(65) Prior Publication Data

US 2020/0261581 A1 Aug. 20, 2020

Related U.S. Application Data

(63) Continuation of application No. 16/249,884, filed on Jan. 16, 2019, now abandoned, which is a continuation of application No. 14/755,297, filed on Jun. 30, 2015, now abandoned, which is a continuation of application No. 13/422,761, filed on Mar. 16, 2012, now Pat. No. 9,072,710.

(51) Int. Cl.
| | | |
|---|---|---|
| A61K 47/02 | (2006.01) |
| A61J 1/06 | (2006.01) |
| A61J 1/10 | (2006.01) |
| A61K 31/192 | (2006.01) |
| A61P 29/00 | (2006.01) |

(52) U.S. Cl.
CPC .............. *A61K 47/02* (2013.01); *A61J 1/065* (2013.01); *A61J 1/10* (2013.01); *A61K 31/192* (2013.01); *A61P 29/00* (2018.01)

(58) Field of Classification Search
CPC ........... A61J 1/065; A61J 1/10; A61K 31/192; A61K 47/02; A61P 29/00; A61P 9/00
See application file for complete search history.

(56) References Cited

U.S. PATENT DOCUMENTS

| | | |
|---|---|---|
| 4,279,926 A | 7/1981 | Bruzzese et al. |
| 4,309,421 A | 1/1982 | Ghyczy et al. |
| 4,569,937 A | 2/1986 | Baker et al. |
| 4,587,252 A | 5/1986 | Arnold |
| 4,690,927 A | 9/1987 | Voss et al. |
| 4,844,907 A | 7/1989 | Elger et al. |
| 4,859,704 A | 8/1989 | Haas |
| 4,861,797 A | 8/1989 | Haas |
| 5,190,947 A | 3/1993 | Riess et al. |
| 5,200,558 A | 4/1993 | Kwan |
| 5,463,117 A | 10/1995 | Stroppolo et al. |
| 6,005,005 A | 12/1999 | Stroppolo et al. |
| 6,342,530 B1 | 1/2002 | Darko |
| 6,423,746 B1 | 7/2002 | Yarbrough et al. |
| 6,727,286 B2 | 4/2004 | Pavliv |
| 8,735,452 B2 | 5/2014 | Pavliv et al. |
| 8,871,810 B2 | 10/2014 | Pavliv et al. |
| 9,012,508 B2 | 4/2015 | Pavliv |
| 9,072,661 B2 | 7/2015 | Pavliv et al. |
| 9,072,710 B2 | 7/2015 | Pavliv et al. |
| 9,114,068 B2 | 8/2015 | Pavliv et al. |
| 9,138,404 B2 | 9/2015 | Pavliv et al. |
| 9,295,639 B2 | 3/2016 | Pavliv et al. |
| 9,649,284 B2 | 5/2017 | Pavliv et al. |
| 9,931,311 B2 | 4/2018 | Pavliv et al. |
| 2003/0100612 A1 | 5/2003 | Pavliv |
| 2003/0191187 A1 | 10/2003 | Lee et al. |
| 2004/0132823 A1 | 7/2004 | Pavliv |
| 2004/0253244 A1 | 12/2004 | Shelton et al. |
| 2006/0142181 A1 | 6/2006 | Miller et al. |
| 2008/0058302 A1 | 3/2008 | Dolle et al. |
| 2008/0077116 A1 | 3/2008 | Dailey et al. |
| 2009/0048345 A1 | 2/2009 | Lee et al. |
| 2009/0054413 A1 | 2/2009 | Henriksson et al. |

(Continued)

FOREIGN PATENT DOCUMENTS

| | | |
|---|---|---|
| CN | 1871028 A | 11/2006 |
| CN | 101217939 A | 7/2008 |

(Continued)

OTHER PUBLICATIONS

Berghaus DE-19912436 Machine English Translation.*
Berghaus DE-19912436 Machine English Translation Claims.*
"Pharmacokinetics & Pharmacodynamics: Dose Selection & the Time Course of Drug Action" by Holford et al., in "Basic & Clinical Pharmacology," 7th Ed., by Katzung (Ed.), Appleton & Lange (Stamford, Connecticut), pp. 34-49 (1998).
"Trial of Caldolor for Treatment of Pain in Post-Operative Adult Patients" ClinicalTrials.com; pp. 1-5; (May 2016).
Advisory Action dated Mar. 9, 2011, issued in connection with corresponding U.S. Appl. No. 12/830,991.
Anonymous: "prescribing information of Caldolor", Jun. 1, 2009, XP55030543, Retrieved from the Internet: URL: http://caldolor.com/pdfs/Prescribing-Information.pdf [retrieved on Jun. 20, 2012].

(Continued)

*Primary Examiner* — Kara R Mcmillian
(74) *Attorney, Agent, or Firm* — VIVICAR LAW, PLLC

(57) ABSTRACT

The present invention provides a pharmaceutical composition comprising an aqueous solution of an ibuprofen solubilizing agent and ibuprofen, the ibuprofen solubilizing agent being in an effective amount such that the ibuprofen in the solution remains soluble at concentrations from 100 mg/mL to 5 mg/mL without undergoing a phase transition. The invention further provides a method of treating a condition chosen from pain, inflammation, fever, and/or patent ductus arteriosis, comprising administering to a patient in need thereof an effective amount of an aqueous solution a ibuprofen solubilizing agent and ibuprofen, the ibuprofen solubilizing agent being in an effective amount such that the ibuprofen in the solution remains soluble at concentrations from 100 mg/mL to 5 mg/mL without undergoing a phase transition, as well as a method for manufacturing the composition.

16 Claims, No Drawings

(56) References Cited

U.S. PATENT DOCUMENTS

| | | |
|---|---|---|
| 2009/0175940 A1 | 7/2009 | Gruber |
| 2009/0264530 A1 | 10/2009 | Nickell |
| 2010/0015237 A1 | 1/2010 | Moses et al. |
| 2010/0234465 A1 | 9/2010 | Pavliv |
| 2011/0028553 A1 | 2/2011 | Pavliv et al. |
| 2011/0028556 A1 | 2/2011 | Pavliv et al. |
| 2011/0028557 A1 | 2/2011 | Pavliv et al. |
| 2011/0028558 A1 | 2/2011 | Pavliv et al. |
| 2013/0225685 A1 | 8/2013 | Atkinson |
| 2015/0335747 A1 | 11/2015 | Pavliv et al. |
| 2017/0273925 A1 | 9/2017 | Pavliv et al. |
| 2017/0281534 A1 | 10/2017 | Pavliv |

FOREIGN PATENT DOCUMENTS

| | | | |
|---|---|---|---|
| CN | 102085179 A | 6/2011 | |
| DE | 19912436 A1 | 9/2000 | |
| JP | H11512081 A | 10/1999 | |
| JP | 2006525960 A | 11/2006 | |
| WO | 9704780 A2 | 2/1997 | |
| WO | 03039532 A1 | 5/2003 | |
| WO | 2004073653 A2 | 9/2004 | |
| WO | 2006126214 A2 | 11/2006 | |
| WO | WO-2011144677 A1 * | 11/2011 | .............. A61P 29/00 |

OTHER PUBLICATIONS

Applicant's Petition filed Jul. 6, 2010, in connection with corresponding U.S. Appl. No. 12/830,991.
Applicant's Preliminary Amendment dated Sep. 27, 2010, filed in connection with corresponding U.S. Appl. No. 12/699,595.
Applicant's Preliminary Amendment dated Sep. 27, 2010, issued in connection with the corresponding U.S. Appl. No. 12/646,499.
Applicant's Response to Notice of Missing Parts dated Feb. 24, 2010, issued in connection with the corresponding U.S. Appl. No. 12/699,595.
Applicant's Response to Office Action dated Aug. 25, 2011, issued in connection with the corresponding U.S. Appl. No. 12/646,499.
Applicant's Response to Office Action dated Aug. 9, 2010, issued in connection with corresponding U.S. Appl. No. 12/830,991.
Applicant's Response to Office Action dated Feb. 4, 2011 filed in connection with corresponding U.S. Appl. No. 12/830,991.
Applicant's Response to Office Action dated Jan. 13, 2010, issued in connection with the corresponding U.S. Appl. No. 12/646,499.
Applicant's Response to Office Action dated Mar. 8, 2012, issued in connection with the corresponding U.S. Appl. No. 12/722,682.
Applicant's Response to Office Action dated Nov. 10, 2010, issued in connection with corresponding U.S. Appl. No. 12/830,991.
Applicant's Response to Office Action dated Oct. 27, 2010 filed in connection with corresponding U.S. Appl. No. 12/830,991.
Applicant's Response to Office Action dated Oct. 28, 2011, issued in connection with corresponding U.S. Appl. No. 12/830,991.
Applicant's Response to Office Action dated Oct. 7, 2011, issued in connection with the corresponding U.S. Appl. No. 12/722,682.
Applicant's Response to Office Action dated Sep. 20, 2011, filed in connection with corresponding U.S. Appl. No. 12/699,595.
Applicant's Response to Office Action dated Sep. 27, 2010 filed in connection with corresponding U.S. Appl. No. 12/830,991.
Applicant's Response to Office Action dated Sep. 28, 2010, issued in connection with corresponding U.S. Appl. No. 12/830,991.
Applicant's Response to Office Action dated Sep. 8, 2010 filed in connection with corresponding U.S. Appl. No. 12/830,991.
Applicant's Response to Office Action dated Sep. 8, 2011, issued in connection with corresponding U.S. Appl. No. 12/830,991.
Applicant's Supplemental Amendment, dated Sep. 27, 2010, in connection with corresponding U.S. Appl. No. 12/830,991.
Applicant's Terminal Disclaimer filed Oct. 27, 2010, in connection with corresponding U.S. Appl. No. 12/830,991.

Bayouth et al. "713: Early Intravenous Ibuprofen Decreases Narcotic Requirement and Length of Stay Following Traumatic Rib Fractures". Grit. Care Med. Dec. 2011; 39(12 Suppl.):199.
Bayouth et al. [Online] Poster Presentation: "713: Early Intravenous Ibuprofen Decreases Narcotic Requirement and Length of Stay Following Traumatic Rib Fractures" [Retrieved Jun. 6, 2013]. Retrieved from the Internet: . Presented at the Society of Critical Care Medicine: 41st Annual Congress, Feb. 4-8, 2012, Houston, Texas. One page.
Boucher, Bradley A., et al., Pharmacokinetic Changes in Critical Illness, Crit Care Clin 22 (2006), pp. 225-271.
Campbell W., et al., "Intravenous diclofenac sodium: does its administration before operation suppress postoperative pain?" Anaesthesia. 1990; 45: 763-6.
Charles Bankhead: "SCCM: IV Ibuprofen Controls Fever in Critically Ill Patients", Internet Citation, Feb. 3, 2009, p. 1, XP008151826, Retrieved from the Internet: URL:http://www.medpagetoday.com/MeetingCoverage/SCCM/12728 [retrieved on May 10, 2012].
Cumberland Pharmaceuticals (Efficacy and Safety Study of Amelior (Caldolor (IV Ibuprofen)) in Hospitalized Adult OrthopedicPatients. NCT00470600 on Jan. 23, 2008.
Davies, Neal M., Clinical Pharmacokinetics of Ibuprofen: The First 30 Years, Clin Pharmacokinet Feb. 1998: 34(2) pp. 101-154.
Dionne, R., et al., "Evaluation of preoperative ibuprofen for postoperative pain after removal of third molars." Oral Surg. Oral Med. Oral Pathol. Jun. 1978;45(6):851-6.
Dionne, R., et al., "Use of Ibuprofen in dentistry" Ibuprofen, A Critical Bibliographic Review, edited by K.D. Rainsford, Chapter 8,2.1., Taylor & Francis, 1999.
European Search Report issued in connection with European App. No. 18183929.1, dated Sep. 27, 2018.
Extended European Search Report for European App. No. 15848484.0, dated Apr. 17, 2018.
Garzon, et al., "Temperature Dependence of Solubility for Ibuprofen in Some Organic and Aqueous Solvents," Journal of Solution Chemistry, 33(11):1379-1395 (2004).
Gordan R. Bernard, et al., The Effect of Ibuprofen on the Physiology and Survival of Patients With Sepsis, The New England Journal of Medicine, vol. 336, No. 13, p. 912-918 (1997).
Grossman, et al., Pathophysiology of Cystic Fibrosis: Implication for critical care Nurses, Crit. Care Nurse, 2005, vol. 25, pp. 46-51.
Hogarth et al "Management of sedation in mechanically ventilated patients", Curr. Opin. Crit. Care vol. 10, 2004, pp. 40-46.
Ibuprofen: Drug Information Provided by Lexi-Comp., Merck Manual Professional, http://www.merck.com/mmpe/print/lexicomp/ibuprofen.html, last accessed Jun. 15, 2011, pp. 1-21 (2010).
International Search Report and Written Opinion dated Jul. 13, 2010 issued in connection with corresponding PCT Patent Application No. PCT/US10/36015.
International Search Report, dated Apr. 1, 2013, issued by the PCT in commonly-owned PCT Application No. PCT/US13/22519.
International Search Report, dated Oct. 25, 2013, issued by the European Patent Office in corresponding EP Application No. 10751461,4.
Interview dated Dec. 6, 2010, issued in connection with corresponding U.S. Appl. No. 12/830,991.
Interview dated May 11, 2011, issued in connection with corresponding U.S. Appl. No. 12/830,991.
JV Aranda, et al., Pharmacokinetics and protein binding of intravenous ibuprofen in the premature newborn infant, Acta Paediatr 86: 289-93, 1997.
Konstan, et al., Ibuprofen in children with cystic fibrosis; pharmacokinetics and adverse effects, J. Pediatr. Jun. 1991, vol. 116, No. 6, pp. 956-964, Abstract.
Lamprecht et al. (Lipid nanocarriers as drug delivery system for ibuprofen in pain treatment. Int J Pharm. Jul. 8, 2004;278(2):407-14).
Maunuksela et al, "Efficacy of rectal ibuprofen in controlling postoperative pain in children" Canadian Journal of Anaesthesia, Mar. 1992, vol. 39, Issue 3, pp. 226-230.
Morris, Peter E., et al., A multi-center, randomized, double-blind, parallel, placebo-controlled trial to evaluate the efficacy, safety, and

(56) References Cited

OTHER PUBLICATIONS pharmacokinetics of intravenous ibuprofen for the treatment of fever in critically ill and non-critically ill adults, Critical Care, 2010, 14:R125, pp. 1-13.
Morris, Peter, et al., A multi-center, randomized, double-blind, placebo-controlled trial of the efficacy and safety of intravenous ibuprofen in febrile adults, Crit Care Med 2008, vol. 36, No. 12 (Suppl), p. A18, Abstract.
Notice of Missing Parts dated Feb. 24, 2010, issued in connection with the corresponding U.S. Appl. No. 12/699,595.
Office Action dated Apr. 16, 2012, issued in connection with corresponding U.S. Appl. No. 12/830,991.
Office Action dated Aug. 25, 2011, issued in connection with the corresponding U.S. Appl. No. 12/646,499.
Office Action dated Aug. 9, 2010 issued in connection with corresponding U.S. Appl. No. 12/830,991.
Office Action dated Jan. 13, 2010, issued in connection with the corresponding U.S. Appl. No. 12/646,499.
Office Action dated Jul. 13, 2011, issued in connection with corresponding U.S. Appl. No. 12/830,991.
Office Action dated Jul. 27, 2012, issued in connection with the corresponding U.S. Appl. No. 12/699,595.
Office Action dated Jul. 9, 2010, issued in connection with corresponding U.S. Appl. No. 12/830,991.
Office Action dated Jun. 14, 2012, issued in connection with corresponding U.S. Appl. No. 12/722,682.
Office Action dated Mar. 18, 2011 issued in connection with the corresponding U.S. Appl. No. 12/570,912.
Office Action dated Mar. 8, 2012, issued in connection with corresponding U.S. Appl. No. 12/722,682.
Office Action dated Mar. 9, 2011 issued in connection with corresponding U.S. Appl. No. 12/830,991.
Office Action dated May 23, 2012, issued in connection with corresponding U.S. Appl. No. 12/646,499.
Office Action dated Nov. 10, 2010 issued in connection with corresponding U.S. Appl. No. 12/830,991.
Office Action dated Oct. 28, 2011, issued in connection with corresponding U.S. Appl. No. 12/830,991.
Office Action dated Sep. 20, 2011, issued in connection with corresponding U.S. Appl. No. 12/699,595.
Office action dated Sep. 28, 2010 issued in connection with corresponding U.S. Appl. No. 12/830,991.
Office Action dated Sep. 8, 2011, issued in connection with corresponding U.S. Appl. No. 12/830,991.
Office Action from corresponding Korean Patent Application No. 10-2011-7023915 dated May 10, 2017.
Office Action issued in connection with corresponding European App. No. 13761444.2, dated Jul. 29, 2016.
Olonisakin, R.P., et al. "Morphine-sparing effect of intravenous paracetamol for post operative pain management following gynaecological surgery," Aft. J. Med. med. Sci., 41:429-436 (2012).
Orlando Regional Medical Center [Online]. "Multi-Modality Pain Control for Rib Fractures" [Retrieved Jun. 6, 2013]. Retrieved from the Internet: Accepted on Nov. 30, 2010. pp. 1-4.
Owen et al. (Ibuprofen in the management of postoperative pain. Br J Anaesth. Dec. 1986;58(12):1371-5).
Payne et al. (The relationship of preoperative and intraoperative factors on the incidence of pain following ambulatory surgery. Ambulatory Surgery. vol. 3, Issue 3, Sep. 1995,abstract).
PCT International Search Report and Written Opinion for PCT/US13/031529, dated Mar. 17, 2014.
PCT International Search Report and Written Opinion for PCT/US15/053987, dated Dec. 22, 2015.
Pharmacokinetic Data, Caldolor® (ibuprofen) Injection, Medical Information: PK, Sep. 1, 2009, Cumberland Pharmaceuticals, pp. 1-8.

Product Information: Caldolor(TM), Jun. 2009.
Ræder, Johan C., et al. "Oral ibuprofen versus paracetamol plus codeine for analgesia after ambulatory surgery." Anesthesia & Analgesia 92.6 (2001): 1470-1472.
Ruth E. Bennie et al: "Postoperative analgesia with preoperative oral ibuprofen on acetaminophen in children undergoing myringotomy", Paediatric Anaestesia, Feb. 12, 1997, pp. 399-403, XP55031201, Retrieved from the Internet: URL:http://onlinelibrary.wiley.com/doi/10.1046/j.1460-9592.1997.d01-115.x/pdf [retrieved on Jun. 27, 2012].
SCCM: IV Ibuprofen Controls Fever in Critically Ill Patients, Feb. 3, 2009.
Shaw, et al. "The Effect of Selected Water-Soluble Excipients on the Dissolution of paracetamol and Ibuprofen," Drug Development and Industrial Pharmacy, 31(6):515-525 (2005).
Sinatra, R S, et al. "Efficacy and safety of single and repeated administration of 1 gram intravenous acetaminophen injection (paracetamol) for pain management after major orthopedic surgery," Anesthesiology, vol. 102:822-831 (2005).
Singla, N., et al., Poster of "A Multi-Center, Randomized, Double-Blind Placebo-Controlled Trial of Intravenous-Ibuprofen (IV-Ibuprofen) for Treatment of Pain in Post-Operative Orthopedic Adult Patients," Presented at the American Academy of Orthopaedic Surgeons (AAOS) Annual Meeting, Mar. 2010.
Singla, N., et al. "A Multi-Center, Randomized, Double-Blind Placebo-Controlled Trial of Intravenous-Ibuprofen (IV-Ibuprofen) for Treatment of Pain in Post-Operative Orthopedic Adult Patients," Pain Med. Aug. 2010; 11(8): 1284-1293.
Soltanzadeh et al., Iran Cardiovasc Res J, 5(3):79-82 (2011).
Southworth et al. "A multicenter, randomized, double-blind, placebo-controlled trial of intravenous ibuprofen 400 and 800 mg every 6 hours in the management of postoperative pain." Clin. Ther. (Sep. 31, 2009).
Stanik-Hutt "Pain management in the critically ill", Critical Care Nurse, vol. 23, No. 2, Apr. 2003, pp. 99-103.
Summary of clinical trial No. NCT00199303 (CiinicaiTrials.gov); Sep. 12, 2005.
Summary of clinical trial No. NCT01 090882 (ClinicaiTrials.gov); Mar. 18, 2010.
Summary of clinical trial No. NCT01552616 (ClinicaiTrials.gov). Feb. 20, 2012.
Summons to attend oral proceedings pursuant to Rule 115(1) from the European Patent Office for European PatentApplication No. 10751461.4 dated Jun. 2, 2017.
Supplementary European Search Report and Written Opinion, dated Jun. 29, 2012, issued in connection with corresponding International Patent Application No. PCT/US10/027096.
Thayeret al. (Effects of ibuprofen on postoperative bowel motility and propulsion. Diseases of the Colon & Rectum 31.5 (1988): 363-367).
Third Party Observations, dated Jul. 25, 2013, issued by the European Patent Office in corresponding EP Application No. 10751461.4.
U.S. Appl. No. 12/699,595, Pavliv.
U.S. Appl. No. 12/722,682, Pavliv.
U.S. Appl. No. 13/356,121, Pavliv.
U.S. Appl. No. 13/422,738, Pavliv.
U.S. Appl. No. 13/422,761, Pavliv.
Van Dyke T et al: "Combination oxycodone 5 mg/ibuprofen 400 mg for the treatment of postoperative pain: A double-blind, placebo- and active-controlled parallel-group study", Clinical Therapeutics, Excerpta Medica, Princeton, NJ, US, vol. 26, No. 12, Dec. 1, 2004, pp. 2003-2014, XP004780661, ISSN: 0149-2918, DOI: 10.1016/J.Clinthera.2004.12.002.
Viitanen et al. "Analgesic efficacy of rectal acetaminophen and ibuprofen alone or in combination for paediatric day-case adenoidectomy." Br. J Anaesth. 2003; vol. 91, pp. 363-367.
Wu et al. "Thoracic Epidural Analgesia versus Intravenous Patient-Controlled Analgesia for the Treatment of Rib Fracture Pain after Motor Vehicle Crash". The Journal of Trauma: Injury, Infection, and Critical Care. 47(3); 1999:564-567.

* cited by examiner

INJECTABLE IBUPROFEN FORMULATION

CROSS-REFERENCE TO RELATED APPLICATIONS

This application is a continuation of U.S. application Ser. No. 16/249,884, filing date Jan. 16, 2019, which is a continuation of U.S. application Ser. No. 14/755,297, filing date Jun. 30, 2015, which is a continuation of U.S. application Ser. No. 13/422,761, filing date Mar. 16, 2012, now U.S. Pat. No. 9,072,710, all of which are hereby incorporated by reference in their entirety.

BACKGROUND OF INVENTION

The present invention relates to a pharmaceutical composition for oral or injectable (parenteral) use containing 2-(4-isobutylphenyl)propionic acid.

2-(4-isobutylphenyl)propionic acid, whose International Nonproprietary Name is ibuprofen, is a well-known anti-inflammatory drug having a molecular weight of 206.28. (Merck Index 12th ed., n4925, page 839). Originally patented in the 1960's, ibuprofen is now marketed generically, as well as under the trade names of Motrin®, Advil®, and Nuprin® for the treatment of pain, inflammation, and fever, and patent ductus arteriosis.

Ibuprofen is readily available as the racemic mixture ((RS)-Ibuprofen) of the two enantiomers, (R)-Ibuprofen and (S)-Ibuprofen. Even though the (S) enantiomer is the biologically active form, most preparations contain the racemic mixture since the (R) enantiomer is converted to the active (S) form in-vivo. For simplicity, hereinafter the term "ibuprofen" will be used to indicate any one of the (R) enantiomer, the (S) enantiomer, or the racemate.

Although ibuprofen has many advantages over other analgesics such as aspirin and acetaminophen, it is very poorly soluble in water. Thus, certain dosage forms of ibuprofen, especially oral or injectable liquids, have been difficult to develop. Several U.S. patents have addressed this problem.

For example, U.S. Pat. No. 4,309,421 appears to describe water-soluble complexes of ibuprofen and phospholipids suitable for parenteral administration. U.S. Pat. Nos. 4,859,704 and 4,861,797 appear to describe the synthesis of alkali metal salts of ibuprofen for preparing a liquid ibuprofen formulation.

Other U.S. patents appear to address this problem by preparing an ibuprofen salt with a basic amino acid as the active pharmaceutical ingredient and then solubilizing the salt to produce a liquid dosage form.

For example, U.S. Pat. No. 5,200,558 appears to describe enhanced analgesic effects of S (+) ibuprofen as salts of L and D amino acids, including arginine, in various dosage forms, including as an injectable solution. U.S. Pat. No. 4,279,926 appears to describe the use of basic amino acid salts of propionic acids for relieving pain and treating inflammatory conditions. Similarly, U.S. Pat. No. 5,463,117 appears to describe the preparation of salts of ibuprofen with basic amino acids. Finally, U.S. Pat. No. 6,005,005 appears to describe a liquid composition for oral use containing ibuprofen and arginine.

However, the approaches described in the patents discussed above have, among others, the disadvantage of requiring the formation of a salt before solubilization, where the salt must be isolated and tested prior to producing the dosage form. Additionally, the ibuprofen formulations resulting from those processes have at least a 1:1 molar ratio of amino acid or base to ibuprofen. It is beneficial from both a cost and development point to not have to form a salt and isolate and test it prior to producing the dosage form. It is also beneficial in most cases to minimize the amount of non-active components, including salts, used in therapeutic products in order to minimize potential side effects. Furthermore, for injectable products it is beneficial to produce a liquid dosage form of ibuprofen having a pH similar to that of blood (pH 7.4). Finally, it is beneficial for an injectable and oral product to have similar pharmacokinetics to minimize the need for dosage adjustments.

U.S. Pat. No. 6,727,286 provides a pharmaceutical composition comprising an aqueous solution of arginine and ibuprofen, wherein the molar ratio of arginine to ibuprofen is less than 1:1, as well as a method of making the same. An embodiment of the '286 patent is a pharmaceutical composition comprising an aqueous solution of arginine and ibuprofen, wherein the molar ratio of arginine to ibuprofen is less than 1:1, and wherein the pH of the solution is less than about 7.8. Another embodiment of the '286 patent is a method of making a pharmaceutical composition comprising an aqueous solution of arginine and ibuprofen, wherein the molar ratio of arginine to ibuprofen is less than 1:1, and wherein the pH of the solution is less than about 7.8. Still other embodiments of the '286 patent are directed to methods of treating pain, inflammation, fever, and/or other conditions alleviated by ibuprofen comprising administering a pharmaceutical composition comprising an aqueous solution of arginine and ibuprofen, wherein the molar ratio of arginine to ibuprofen is less than 1:1, and wherein the pH of the solution is less than about 7.8.

The '286 patent covers the Assignee's present commercial formulation of ibuprofen injection for intravenous use, sold under the trade name Caldolor®. Caldolor® is indicated in adults for the management of mild to moderate pain and the management of moderate to severe pain as an adjunct to opioid analgesics, and is commercially available as a 400 mg/4 mL single-dose vial (100 mg/mL) and 800 mg/8 mL single-dose vial (100 mg/mL). Appropriate diluents include 0.9% Sodium Chloride Injection USP (normal saline), 5% Dextrose Injection USP (D5W), or Lactated Ringers Solution. The recommendation for diluting both strengths is to dilute in 250 mL of diluent.

OBJECTS AND SUMMARY OF THE INVENTION

It is an object of the present invention to solubilize ibuprofen during the manufacture of a ibuprofen solution suitable for injection, wherein the ibuprofen in the solution remains soluble at concentrations from about 100 mg/mL to about 5 mg/mL, and preferably to about 4 mg/mL, without undergoing a phase transition, e.g., without turning hazy and/or precipitating.

It is another object of the present invention to utilize an ibuprofen solubilizing agent to solubilize ibuprofen during the manufacture of the pharmaceutical product instead of using a salt form of ibuprofen, where the ibuprofen solubilizing agent provides an ibuprofen solution in which the ibuprofen is soluble in the solution from a concentration of about 100 mg/mL to a concentration of about 5 mg/ML, and preferably to about 4 mg/mL, without turning hazy or precipitating at intermediate concentrations between 100 mg/ML and 5 mg/mL.

It is another object of the present invention to provide a pharmaceutical composition comprising an aqueous solution of an ibuprofen solubilizing agent and ibuprofen, wherein the molar ratio of the ibuprofen solubilizing agent to ibuprofen is less than or equal to about 1:1, where the ibuprofen solubilizing agent provides an ibuprofen solution in which the ibuprofen is soluble in the solution from a concentration of about 100 mg/mL to a concentration of about 5 mg/mL, and preferably to about 4 mg/mL, without undergoing a phase transition, e.g, turning hazy and/or precipitating at intermediate concentrations between 100 mg/ML and 5 mg/mL.

It is another object of the invention to provide a pharmaceutical composition comprising an aqueous solution of an ibuprofen solubilizing agent and ibuprofen which provides an effective dose of ibuprofen, e.g., from about 400 mg to about 800 mg, in a smaller volume of solution, e.g., 40-50 mL (400 mg dose) and 80 mL-100 mL (800 mg dose).

In accordance with the above objects and others, the present invention is directed in part to a pharmaceutical composition comprising an aqueous solution of an ibuprofen solubilizing agent and ibuprofen, the ibuprofen solubilizing agent being in an effective amount such that the ibuprofen in the solution remains soluble at concentrations from 100 mg/ML to 5 mg/ML, and preferably to about 4 mg/mL, without undergoing a phase transition, e.g, turning hazy and/or precipitating. In certain preferred embodiments, the ibuprofen solubilizing agent is in a molar ratio to ibuprofen of less than or equal to about 1:1.

In preferred embodiments, the pharmaceutical composition is sterile filtered or terminally sterilized.

In certain preferred embodiments, the ibuprofen solubilizing agent is sodium phosphate or potassium phosphate, and the molar ratio of the ibuprofen solubilizing agent to the ibuprofen is from about 0.7 to about 0.9:1. The molar ratio of the sodium or potassium phosphate to ibuprofen is preferably about 0.9:1.

In other embodiments, the ibuprofen solubilizing agent is sodium carbonate or potassium carbonate, and the molar ratio of the ibuprofen solubilizing agent to the ibuprofen is from about 0.6:1 to about 0.9:1.

In yet other embodiments, the ibuprofen solubilizing agent is sodium hydroxide, and the molar ratio of the ibuprofen solubilizing agent to the ibuprofen is about 1.05:1.

In yet further embodiments, the ibuprofen solubilizing agent is L-lysine, and the molar ratio of the ibuprofen solubilizing agent to the ibuprofen is about 1:1.

In certain embodiments, the invention is directed to a pharmaceutical composition comprising an aqueous solution of ibuprofen and sodium hydroxide, L-lysine, L-arginine, sodium carbonate, potassium carbonate, sodium phosphate, potassium phosphate in a molar ratio to ibuprofen of about 1.05:1 or more, the ibuprofen solubilizing agent being in an effective amount such that the ibuprofen in the solution remains soluble at concentrations from 100 mg/ML to 5 mg/ML, and preferably to about 4 mg/mL, without undergoing a phase transition, e.g, turning hazy and/or precipitating.

The pharmaceutical composition may be stored in pre-filled bags, e.g., polyolefin or polyvinyl chloride (PVC) bags. The pharmaceutical composition may also be stored in a container selected from a bag, a vial, or a bottle. In certain embodiments, the container is made from a flexible material such as a plastic, polypropylene, polyolefin, or PVC, or another pharmaceutically acceptable polymeric material or glass.

The ibuprofen used in the compositions and methods of the invention may be (RS)-Ibuprofen, or (S)-Ibuprofen.

In preferred embodiments, the pharmaceutical compositions of the invention have a pH from about 6.8 to about 10.0, and in certain preferred embodiments from about 7.0 to about 7.8. In certain embodiments, the pH of the aqueous solution of ibuprofen is about 6.8, 7.0, about 7.2, about 7.4, about 7.6, about 7.7, about 7.8, about 8.0, about 8.2, about 8.4, about 8.6, about 8.8 about 9.0, about 9.2, about 9.4, about 9.6, about 9.8, or about 10.0.

In other embodiments, the invention is directed to a method of treating a condition chosen from pain, inflammation, fever, and/or patent ductus arteriosis, comprising administering to a patient in need thereof an effective amount of an aqueous solution an ibuprofen solubilizing agent and ibuprofen, the ibuprofen solubilizing agent being in an effective amount such that the ibuprofen in the solution remains soluble at concentrations from 100 mg/mL to 5 mg/mL without undergoing a phase transition, e.g., turning hazy and/or precipitating. In preferred embodiments, the pharmaceutical compositions of the invention have a pH from about 6.8 to about 10.0. In certain preferred embodiments, the pH of the aqueous solution of ibuprofen is from about 7.0 to about 7.8. The administration is preferably via intravenous injection, but can also be via intramuscular injection or orally.

In certain preferred embodiments, the dose of ibuprofen administered to the patient comprises from about 100 mg to about 800 mg of ibuprofen. In certain embodiments, the effective amount is about 400 mg of ibuprofen. In certain preferred embodiments, the effective amount of the aqueous solution comprises about 800 mg ibuprofen. In other embodiments, the effective amount is about 7.5 mg/kg of ibuprofen.

In certain embodiments of the invention, the condition being treated in the patient is pain. In other embodiments, the condition is inflammation. In other embodiments, the condition is fever. In other embodiments, the condition is patent ductus arteriosis. In further embodiments, the patient is a critically ill patient receiving at least one treatment selected from vasopressor support and mechanical ventilation. In certain embodiments where the patient is a critically ill, the patient is further being treated by one or more of the following: the patient is being administered large volumes of blood products; is undergoing dialysis; is receiving multiple antibiotics; and/or the patient has a pulmonary artery catheter or an arterial blood pressure catheter inserted.

In certain preferred embodiments, the method of treatment comprises administering the aqueous solution of ibuprofen intravenously from a bag made of a flexible material such as a plastic, polypropylene, polyolefin, and PVC, or another pharmaceutically acceptable polymeric material. In other embodiments, the aqueous solution of ibuprofen is contained, e.g., in a bottle or vial made from, e.g., plastic or glass.

In other preferred embodiments, the invention is directed to a method of treating one or more conditions chosen from pain, inflammation, fever, and patent ductus arteriosis comprising administering to a patient in need thereof an aqueous solution comprising an effective dose of ibuprofen together with an effective amount of an ibuprofen solubilizing agent selected from sodium phosphate and potassium phosphate, wherein the molar ratio of ibuprofen solubilizing agent to ibuprofen is from about 0.65:1 to about 0.9:1, preferably about 0.7:1 to about 0.9:1.

In other embodiments, the invention is directed to a method of treating one or more conditions chosen from pain, inflammation, fever, and patent ductus arteriosis comprising administering to a patient in need thereof an aqueous solution comprising an effective dose of ibuprofen together with an effective amount of an ibuprofen solubilizing agent selected from sodium carbonate and potassium carbonate, wherein the molar ratio of ibuprofen solubilizing agent to ibuprofen is from about 0.6:1 to about 0.9:1.

In yet other embodiments, the invention is directed to a method of treating one or more conditions chosen from pain, inflammation, fever, and patent ductus arteriosis comprising administering to a patient in need thereof an aqueous solution comprising an effective dose of ibuprofen together with L-lysine in a molar ratio to ibuprofen of about 1:1.

In yet other embodiments, the invention is directed to a method of treating one or more conditions chosen from pain, inflammation, fever, and patent ductus arteriosis comprising administering to a patient in need thereof an aqueous solution comprising an effective dose of ibuprofen together with sodium hydroxide in a molar ratio to ibuprofen of about 1.05:1.

The invention is further directed in part to a pharmaceutical composition comprising an effective dose of ibuprofen together with an effective amount of an ibuprofen solubilizing agent in an effective amount such that the ibuprofen in the solution remains soluble at concentrations from 100 mg/mL to 5 mg/mL without undergoing a phase transition, e.g., without turning hazy and/or precipitating, and the concentration of ibuprofen in the aqueous solution is from about 1 mg/mL to about 100 mg/mL, the aqueous solution being contained in a bag, or a glass or plastic vial or bottle. In certain embodiments, the pH of the aqueous solution of ibuprofen is from about 6.8 to about 10.0. In certain preferred embodiments, the pH of the aqueous solution of ibuprofen is from about 7.0 to about 7.8. In further preferred embodiments, the aqueous solution is at a concentration of 10 mg/mL and is contained in the bag at a volume of 80 mL or 40 mL. In further embodiments, the aqueous solution contained in the bag has an ibuprofen concentration of 8 mg/mL and is contained in the bag at a volume of 100 mL or 50 mL.

In further embodiments, the invention is directed to a pharmaceutical composition comprising an aqueous solution of ibuprofen and an ibuprofen solubilizing agent selected from sodium carbonate and potassium carbonate, wherein the molar ratio of ibuprofen solubilizing agent to ibuprofen is from about 0.6:1 to about 0.9:1.

In further embodiments, the pharmaceutical composition may comprise an aqueous solution of ibuprofen and L-lysine in a molar ratio to ibuprofen of about 1:1.

In further embodiments, the pharmaceutical composition may comprise an aqueous solution of ibuprofen together and sodium hydroxide in a molar ratio to ibuprofen of about 1.05:1.

In certain preferred embodiments, the invention is directed to a pharmaceutical composition comprising an aqueous solution of ibuprofen and an ibuprofen solubilizing agent selected from sodium phosphate and potassium phosphate, wherein the molar ratio of ibuprofen solubilizing agent to ibuprofen is from about 0.65:1 to about 0.9:1, preferably about 0.7:1 to about 0.9:1. In certain preferred embodiments, the ibuprofen solubilizing agent is sodium phosphate in a molar ratio to ibuprofen of about 0.9:1. In certain preferred embodiments, the ibuprofen solubilizing agent is potassium phosphate in a molar ratio to ibuprofen of about 0.9:1.

In any of the foregoing, the pharmaceutical composition may comprise an effective dose of ibuprofen, e.g., a dose selected from 400 mg and 800 mg.

With respect to the pharmaceutical compositions of the present invention, these compositions preferably are stable. In certain preferred embodiments, the pharmaceutical compositions of the invention show no detectable chemical degradation after incubation for one month at 40° C. In addition, or alternatively, the pharmaceutical compositions can be stored at ambient conditions in prefilled polyolefin bags and remains clear and colorless for at least about 12 weeks. In addition, or alternatively, the pharmaceutical compositions can be stored in a bag made from a pharmaceutically acceptable polymer for at least about 12 weeks at 4° C. In addition, or alternatively, the pharmaceutical compositions can be stored in a bag made from a pharmaceutically acceptable polymeric material for at least about 12 weeks at 25° C. Preferably, the pharmaceutical compositions remain clear and colorless when stored in a bag made from a pharmaceutically acceptable polymer and exposed to at least one freeze-thaw cycle.

In certain preferred embodiments, the aqueous solution comprises ibuprofen in a concentration from about 1 mg/mL to about 100 mg/mL. In certain preferred embodiments, the aqueous solution comprises ibuprofen in a concentration of about 10 mg/mL. In certain preferred embodiments, the aqueous solution contained in the bag is 80 mL at an ibuprofen concentration of 10 mg/mL. In other preferred embodiments, the aqueous solution contained in the bag is 40 mL at an ibuprofen concentration of 10 mg/mL. In certain preferred embodiments, the aqueous solution contained in the bag has an ibuprofen concentration of 8 mg/mL and a volume selected from 100 mL or 50 mL.

In certain preferred embodiments, the invention is directed to a method of treating one or more conditions chosen from pain, inflammation, fever, and patent ductus arteriosis comprising intravenously administering to a patient in need thereof an aqueous solution comprising an effective dose of ibuprofen together with an effective amount of an ibuprofen solubilizing agent selected from sodium phosphate and potassium phosphate, wherein the molar ratio of ibuprofen solubilizing agent to ibuprofen is from about 0.65:1 to about 0.9:1, preferably about 0.7:1 to about 0.9:1 and the concentration of ibuprofen in the aqueous solution is from about 1 mg/mL to about 100 mg/mL. In certain embodiments, the method further comprises administering an 800 mg dose of ibuprofen to the patient. In other embodiments, the method further comprises administering a 400 mg dose of ibuprofen to the patient. In certain embodiments, the ibuprofen solubilizing agent is sodium phosphate. In certain other embodiments, the ibuprofen solubilizing agent is potassium phosphate. In certain preferred embodiments, the pH of the aqueous solution of ibuprofen is from about 7.0 to about 7.8. In certain preferred embodiments, the molar ratio of ibuprofen solubilizing agent to ibuprofen is about 0.9:1.

The invention is further directed in part to a pharmaceutical composition comprising an effective dose of ibuprofen together with an effective amount of a tribasic phosphate salt as an ibuprofen solubilizing agent (e.g., sodium phosphate, potassium phosphate, or mixtures thereof) wherein the molar ratio of ibuprofen solubilizing agent to ibuprofen is from about 0.65:1 to about 0.9:1, preferably from about 0.7:1 to about 0.9:1 and the concentration of ibuprofen in the aqueous solution is from about 1 mg/mL to about 100 mg/mL, the aqueous solution being contained in a bag made from a material selected from polypropylene, polyolefin and polyvinylchloride. In certain preferred embodiments, the pH of the aqueous solution of ibuprofen is from about 7.0 to about 7.8. In further preferred embodiments, the aqueous solution is at a concentration from about 5 mg/mL to about 15 mg/mL, preferably from about 5 mg/mL to about 10 mg/mL, and is contained in the bag, e.g., at a volume of 80 mL or 40 mL (e.g., for an aqueous ibuprofen solution comprising ibuprofen at a 10 mg/mL concentration). In further embodiments, the aqueous solution contained in the bag has an ibuprofen concentration of 8 mg/mL and is contained in the bag at a volume of 100 mL or 50 mL.

Certain preferred embodiments of the invention are directed to a pre-filled bag for intravenous administration, comprising a pharmaceutically effective dose (e.g., 400 mg or 800 mg) of ibuprofen and an ibuprofen solubilizing agent selected from sodium phosphate, potassium phosphate and mixtures thereof, the ibuprofen solubilizing agent being in a molar ratio to ibuprofen from about 0.7:1 to about 0.9:1, and the concentration of ibuprofen in the aqueous solution being from about 5 mg/mL to about 15 mg/mL. The aqueous ibuprofen remains physically and chemically stable in the pre-filled bag for intravenous administration for time period suitable to provide a useful shelf-life of the product (e.g., 12 months, 24 months, 36 months, 48 months, 60 months).

The invention is further directed in part to a method of preparing an aqueous solution of ibuprofen suitable for intravenous injection, comprising adding the ibuprofen solubilizing agent to water, mixing until the ibuprofen solubilizing agent is dissolved to form an aqueous solution of the ibuprofen solubilizing agent, adding ibuprofen to the solution, and mixing until the ibuprofen is dissolved to form the aqueous solution of ibuprofen solubilizing agent and ibuprofen, such that the ibuprofen solubilizing agent maintains the ibuprofen soluble in the aqueous solution at concentrations from 100 mg/mL to 5 mg/mL without undergoing a phase transition, e.g., without turning hazy and/or precipitating. In certain embodiments, the method further comprises optionally adding sufficient water to result in the desired concentration of ibuprofen. In certain preferred embodiments, the method further comprises filtration to remove any possible particulate matter and remove possible microbial contamination, rendering it sterile. The product may also be sterilized by means of terminal sterilization (heat or irradiation). In certain further embodiments, the method further comprises adjusting the pH of the aqueous solution to a pH from about 6.8 to about 10.0, and in certain embodiments from about 7.0 to about 7.8, using, e.g., any of the methods described herein.

For the purposes of the present invention, the phrase "without undergoing a phase transition" means that the aqueous solution of ibuprofen and ibuprofen solubilizing agent does not turn hazy and/or there is substantially no precipitate in the solution.

DETAILED DESCRIPTION OF THE INVENTION

While the aqueous formulations described in the '286 patent provide pharmaceutically acceptable aqueous solutions ibuprofen, it has been found that there are several limitations to that product. One such limitation is that the ibuprofen contained in aqueous ibuprofen formulations which comprise arginine and ibuprofen at a molar ratio of 0.92:1 are soluble at a concentration of 100 mg/mL to about 20 or 25 mg/mL, but thereafter go through a phase transition where the ibuprofen is not soluble and precipitates out of solution, until the solution is further diluted to a concentration of approximately 4-5 mg ibuprofen/mL. It has also recently been discovered that the product may precipitate in polyolefin IV bags.

The present invention overcomes the limitations of the aqueous ibuprofen solutions comprised of arginine as an ibuprofen solubilizing agent together with ibuprofen. Thus, the present invention is directed in part to pharmaceutical compositions comprising an aqueous solution of ibuprofen together with an effective amount of an ibuprofen solubilizing agent such that the ibuprofen in the solution remains soluble at concentrations from 100 mg/mL to 5 mg/mL without undergoing a phase transition, e.g., without turning hazy and/or precipitating. Suitable ibuprofen solubilizing agents include, but are not limited to, sodium and potassium phosphate, sodium and potassium carbonate, sodium hydroxide, and L-lysine, at molar concentrations relative to the ibuprofen such that the resultant aqueous ibuprofen solution remains soluble at concentrations from 100 mg/mL to 5 mg/mL without undergoing a phase transition. A further suitable ibuprofen solubilizing agent is L-arginine at a molar ratio to ibuprofen greater than about 1.05:1.

In preferred embodiments, the molar ratio of ibuprofen solubilizing agent to ibuprofen in the pharmaceutical composition is less than 1:1. Certain other embodiments of the invention are directed to pharmaceutical compositions comprising an aqueous solution of an ibuprofen solubilizing agent and ibuprofen which have a molar ratio of ibuprofen solubilizing agent to ibuprofen greater than 1:1, with the proviso that the ibuprofen in the solution remains soluble at concentrations from 100 mg/mL to about 5 mg/mL, preferably to about 4 mg/mL, without undergoing a phase transition, e.g., turning hazy and/or precipitating. In preferred embodiments, the pH of the aqueous solution of ibuprofen is from about 7.0 to about 7.8.

Pharmaceutical compositions comprising an aqueous solution of ibuprofen and an ibuprofen solubilizing agent selected from sodium carbonate and potassium carbonate preferably have a molar ratio of ibuprofen solubilizing agent to ibuprofen is from about 0.6:1 to about 0.9:1. Pharmaceutical compositions comprising an aqueous solution of ibuprofen and L-lysine preferably have a molar ratio of L-lysine to ibuprofen of about 1:1. Pharmaceutical compositions comprising an aqueous solution of ibuprofen and sodium hydroxide preferably have a molar ratio of sodium hydroxide to ibuprofen of about 1.05:1. Pharmaceutical compositions comprising an aqueous solution of ibuprofen and L-arginine preferably have a molar ratio of L-arginine to ibuprofen of about 1.05:1 or greater. Pharmaceutical compositions comprising an aqueous solution of ibuprofen and an ibuprofen solubilizing agent selected from sodium phosphate and potassium phosphate preferably have a molar ratio of ibuprofen solubilizing agent to ibuprofen from about 0.7:1 to about 0.9:1.

The present inventor has further discovered that a liquid composition of ibuprofen can be produced by combining ibuprofen with the ibuprofen solubilizing agents of the invention at molar ratios that minimize the amount of ibuprofen solubilizing agent(s) necessary to solubilize the ibuprofen, and that achieve a composition having a pH that is suitable for injection. Thus, another embodiment of the invention is a pharmaceutical composition comprising an aqueous solution of ibuprofen, wherein the pH is from about 6.8 to about 10.0. In yet another embodiment of the invention, the pharmaceutical composition comprises an aqueous solution of ibuprofen, wherein the pH is from about 7.0 to about 7.8. A further embodiment of the invention is a pharmaceutical composition comprising an aqueous solution of ibuprofen, wherein the pH is about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, or about 10.0.

The present inventor has further discovered a method of making a pharmaceutical composition comprising an aqueous solution of ibuprofen and an ibuprofen solubilizing agent that maintains the ibuprofen soluble in the aqueous solution at concentrations from 100 mg/mL to 5 mg/mL without undergoing a phase transition, e.g., without turning hazy and/or precipitating, wherein the method comprises the following: adding the ibuprofen solubilizing agent to water, mixing until the ibuprofen solubilizing agent is dissolved to form an aqueous solution of the ibuprofen solubilizing agent, adding ibuprofen to the solution, and mixing until the ibuprofen is dissolved to form the aqueous solution of ibuprofen solubilizing agent and ibuprofen, optionally adding sufficient water to result in the desired concentration of ibuprofen. The pH of the resulting solution can be adjusted using techniques known in the art to achieve a desired pH, for example a pH similar to that of blood. The resulting product is a clear, colorless solution that can readily be passed through a 0.2 micron filter. Finally, the resulting solution can be terminally sterilized or lyophilized.

Alternatively, the ibuprofen can be added prior to the ibuprofen solubilizing agent, or the ibuprofen solubilizing agent and ibuprofen can be added at the same time. Moreover, the pH of the solution can be adjusted by adding additional ibuprofen solubilizing agent or ibuprofen to achieve the desired pH. For example, in one embodiment of the invention, an aqueous solution of ibuprofen solubilizing agent and ibuprofen is prepared that results in a molar ratio of less than 1:1, and then additional ibuprofen solubilizing agent is added to achieve a pH of about 6.8 to about 10.0, and in certain embodiments preferably a pH from about 7.0 to about 7.8.

The present inventor has further discovered a method of treating a condition chosen from pain, inflammation, fever, and/or other conditions alleviated by ibuprofen comprising administering to a patient in need thereof an effective amount of a pharmaceutical composition comprising an aqueous solution of ibuprofen solubilizing agent and ibuprofen, as described herein. Additionally, the present inventor has discovered a method of treating a condition chosen from pain, inflammation, fever, and/or other conditions alleviated by ibuprofen comprising administering to a patient in need thereof an effective amount of a pharmaceutical composition comprising an aqueous solution of ibuprofen solubilizing agent and ibuprofen, wherein pH of the aqueous solution from about 6.8 to about 10.0. Other conditions alleviated by ibuprofen include, but are not limited to, patent ductus arteriosis and certain forms of cancer. In certain embodiments, the patient is a critically ill patient receiving at least one treatment selected from vasopressor support and mechanical ventilation. In certain embodiments, the patient is a critically ill patient selected from the group consisting of a patient who is being administered large volumes of blood products; is undergoing dialysis; is receiving multiple antibiotics; has a pulmonary artery catheter or an arterial blood pressure catheter inserted; and combinations of any of the foregoing.

The pharmaceutical composition may be administered by injection (intravenous or intramuscular) or orally. Dosages of the pharmaceutical composition range from about 5 mg to about 1000 mg of ibuprofen in the pharmaceutical composition and can be determined by one of ordinary skill in the art. In one embodiment, the dosage is from about 100 to about 800 mg of ibuprofen in the pharmaceutical composition. In a further embodiment, the dosage is about 400 mg of ibuprofen in the pharmaceutical composition. In still another embodiment, the dosage of the pharmaceutical composition is from about 5 to about 10 mg/kg, and in a further embodiment the dosage of the pharmaceutical composition is about 7.5 mg/kg.

In certain preferred embodiments, the pharmaceutical composition (e.g., aqueous solution of ibuprofen) may include ibuprofen at a concentration of from about 1 mg/mL to about 100 mg/mL, and in certain preferred embodiments about 10 mg/mL. The aqueous ibuprofen solution may be filled, e.g., at 80 mL at 10 mg/mL for a 800 mg ibuprofen dose and 40 mL for a 800 mg ibuprofen dose. Alternatively, an 8 mg/mL ibuprofen concentration filled at either 100 mL or 50 mL is contemplated for a 800 mg ibuprofen dose and a 400 mg ibuprofen dose, respectively. Obvious variations of concentrations and volumes of ibuprofen providing pharmaceutically acceptable doses of ibuprofen would be contemplated by one having ordinary skill in the art, and are encompassed by the present specification and the appended claims.

Certain embodiments of the invention are directed to the aqueous ibuprofen solution in pharmaceutically acceptable containers, which may be sterilized prior to labeling and secondary packaging. The product can be sterile filtered or terminally sterilized. The containers may or may not have an overwrap, if needed to minimize water loss through the plastic. The product can be stored at ambient conditions and shipped to hospitals in prefilled bags. The container is preferably a bag made of polypropylene, polyolefin, PVC, or other pharmaceutically acceptable polymeric materials. The product can also be filled into glass or plastic bottles and infused into patients.

In certain preferred embodiments, the ibuprofen solubilizing agent is a tribasic phosphate, most preferably sodium or potassium phosphate. The tribasic phosphates solubilize ibuprofen at less than a 1:1 molar ratio. In contrast, dibasic phosphates do not solubilize ibuprofen. The tribasic phosphates have unique beneficial properties as compared to arginine, including the fact that aqueous solutions of ibuprofen which utilize tribasic phosphate salts as ibuprofen solubilizing agents as set forth herein do not go through phase transition and precipitate at ibuprofen concentrations between, e.g., 100 mg/mL and 5 mg/mL (or less), and are soluble at all ranges from the maximum solubility down through less than 4 mg/mL. The product is also compatible with all IV bag materials with no evident precipitation, including forced freeze thaws. These are very important features with respect to containing an aqueous solution of ibuprofen as described herein in a pre-filled bag, e.g, at an ibuprofen concentration between 5 mg/mL and about 15 mg/mL, or between about 5 mg/mL and 10 mg/mL. The higher ibuprofen concentration in solution in the pre-filled bag, e.g., 8 to 10 mg/mL (as compared to 3.24 mg/mL typically used for the commercially available Caldolor® product) allows for significantly reduced volume (better patient safety, children, fluid restricted patients, etc), and allows such pre-filled bag products to constitute small volume parenterals.

DETAILED DESCRIPTION OF PREFERRED EMBODIMENTS

The following examples represent specific embodiments of the foregoing discovery, but are not representative of the entire scope of the invention. The ibuprofen and ibuprofen solubilizing agents used in the examples are United States Pharmacopeia grade, but other pharmaceutically acceptable ibuprofen solubilizing agents can be utilized.

Example 1

Manufacture of Ibuprofen/$Na_3PO_4$ Solution

An ibuprofen formulation comprising sodium phosphate ($Na_3PO_4$) in a molar ratio of phosphate salt to ibuprofen of 0.9:1 is prepared as follows:
1. 7.15 kg of $Na_3PO_4$ are added, mixed and dissolved in 125 kg of water for injection.
2. 10 kg of ibuprofen are added, mixed and dissolved in the sodium phosphate solution from step 1.
3. 3.5 kg of sodium chloride are added, mixed and dissolved in ibuprofen/phosphate solution from step 2.
4. Water for injection is added to achieve a final weight of 1000 kg.
5. The solution is passed through a 0.2 micron filter and filled into the appropriate container.
6. The containers may be terminally sterilized prior to labeling and secondary packaging.

Example 2

Manufacture of Ibuprofen/$K_3PO_4$ Solution

An ibuprofen formulation comprising potassium phosphate ($K_3PO_4$) in a molar ratio of phosphate salt to ibuprofen of 0.9:1 is prepared as follows:
1. 9.26 kg of $K_3PO_4$ are added, mixed and dissolved in 125 kg of water for injection.
2. 10 kg of ibuprofen are added, mixed and dissolved in the sodium phosphate solution from step 1.
3. 2.5 kg of sodium chloride are added, mixed and dissolved in ibuprofen/phosphate solution from step 2.
4. Water for injection is added to achieve a final weight of 1000 kg.
5. The solution is passed through a 0.2 micron filter and filled into the appropriate container.
6. The containers may be terminally sterilized prior to labeling and secondary packaging.

Example 3

Solubility of Ibuprofen with Sodium and Potassium Phosphate

Ibuprofen (IBU) was completely dissolved at 70 mg/mL when sodium phosphate tribasic ($Na_3PO_4$) (Table 1) was used and up to 100 mg/mL when potassium phosphate tribasic ($K_3PO_4$) (Table 2) was used. The molar ratios of $PO_4$ to IBU were 0.7:1.0 to 0.9:1.0. The IBU solutions were all clear and colorless at each concentration tested with both $Na_3PO_4$ and $K_3PO_4$ (Tables 1 and 2).

TABLE 1

| | Solubility of IBU with $Na_3PO_4$ | | | | | |
|---|---|---|---|---|---|---|
| Molar Ratio | $Na_3PO_4$ | | | | | |
| Concentration | 0.7:1.0 | | 0.8:1.0 | | 0.9:1.0 | |
| (mg/mL) | Appearance | pH | Appearance | pH | Appearance | pH |
| 70 | Clear and colorless | 7.21 | Clear and colorless | 7.53 | Clear and colorless | — |
| 16 | Clear and colorless | 7.07 | Clear and colorless | 7.40 | Clear and colorless | 7.42 |
| 8 | Clear and colorless | 7.13 | Clear and colorless | 7.52 | Clear and colorless | 7.35 |
| 4 | Clear and colorless | 7.19 | Clear and colorless | 7.60 | Clear and colorless | 7.33 |

TABLE 2

| | Solubility of IBU with $K_3PO_4$ | | | | | |
|---|---|---|---|---|---|---|
| Molar Ratio | $K_3PO_4$ | | | | | |
| Concentration | 0.7:1.0 | | 0.8:1.0 | | 0.9:1.0 | |
| (mg/mL) | Appearance | pH | Appearance | pH | Appearance | pH |
| 100 | Clear, colorless | 7.13 | Clear, colorless | 7.34 | Clear, colorless | |
| 25 | Slight, White haze | 6.88 | Clear, colorless | 7.02 | Clear, colorless | 7.20 |
| 10 | Clear, colorless | 6.74 | Clear, colorless | 7.07 | Clear, colorless | 7.27 |
| 8 | Clear, colorless | 6.77 | Clear, colorless | 7.09 | Clear, colorless | 7.37 |
| 4 | Clear, colorless | 6.83 | Clear, colorless | 7.16 | Clear, colorless | 7.38 |
| 3.2 | Clear, colorless | 6.85 | Clear, colorless | 7.18 | Clear, colorless | 7.40 |

Example 4

Physical Stability of Ibuprofen Formulations Containing Sodium Phosphate and Potassium Phosphate Ibuprofen ("IBU") formulations containing $Na_3PO_4$ and $K_3PO_4$ were further tested for physical and chemical stability. First, the physical stability of Ibuprofen/phosphate formulations ("IBU:$PO_4$") at different ibuprofen concentrations (4 mg/mL, 8 mg/mL and 16 mg/mL) with the ibuprofen:phosphate in a molar ratio of 1.0:0.85, in IntraVia® IV bags from Baxter was tested. The results are set forth in Table 3 below:

TABLE 3

Physical Stability of IBU:$PO_4$ formulations at 4, 8, and 16 mg/mL

| Sample | Conc. (mg/mL) | Freeze-Thaw Cycles 1 | 2 | 3 | 4° C. 12 weeks | 25° C. 12 weeks |
|---|---|---|---|---|---|---|
| IBU: $K_3PO_4$ (1.0:0.85) | 16 | Clear, colorless | Clear, colorless | Clear, colorless | Clear, colorless | Clear, colorless |
|  | 8 | Clear, colorless | Clear, colorless | Clear, colorless | Clear, colorless | Clear, colorless |
|  | 4 | Clear, colorless | Clear, colorless | Clear, colorless | Clear, colorless | Clear, colorless |
| IBU: $Na_3PO_4$ (1.0:0.85) | 16 | Clear, colorless | Clear, colorless | Clear, colorless | Clear, colorless | Clear, colorless |
|  | 8 | Clear, colorless | Clear, colorless | Clear, colorless | Clear, colorless | Clear, colorless |
|  | 4 | Clear, colorless | Clear, colorless | Clear, colorless | Clear, colorless | Clear, colorless |

The results show that each of the formulations remained clear and colorless under each of the conditions tested, i.e., 1-3 freeze-thaw cycles, and storage at 4° C. for 12 weeks and storage at 25° C. for 12 weeks.

Ibuprofen ("IBU") formulations containing $Na_3PO_4$ were further tested for physical stability at an ibuprofen concentration of 10 mg/mL with the ibuprofen:phosphate in a molar ratio of 1.0:0.9 in different types of IV bags: IntraVia® (Baxter), Technoflex® (Technoflex), and PAB® (Braun). The results are shown in Table 4.

TABLE 4

Physical Stability in Different Types of IV Bags

| Sample | IV bag | Freeze-Thaw Cycles 1 | 2 | 3 | 4° C. 12 days | 25° C. 12 days |
|---|---|---|---|---|---|---|
| 10 mg/mL IBU: $Na_3PO_4$ (1.0:0.9) | Intra-Via® | Clear, colorless | Clear, colorless | Clear, colorless | Clear, colorless | Clear, colorless |
|  | Techno-flex® | Clear, colorless | Clear, colorless | Clear, colorless | Clear, colorless 2 days | Clear, colorless 2 days |
|  | PAB® | Clear, colorless | — | — | Clear, colorless | Clear, colorless |

The results show that the formulation remained clear and colorless in each of the different IV bags tested.

Example 5

Chemically Stability of Ibuprofen Formulations Containing Potassium Phosphate The chemical stability of formulations at 10 mg/mL IBU with $K_3PO_4$ with a molar ratio of 0.82:1.0 ($K_3PO_4$:IBU) was determined. Samples were filled into 3 mL glass vials, stoppered with rubber septa, and capped and then either autoclaved or stored at 40 and 50° C. for 1 month. The results are set forth in Table 5 below.

TABLE 5

Chemical stability of 10 mg/mL IBU dissolved in $K_3PO_4$.

| To | | | | After Autoclaving | | | |
|---|---|---|---|---|---|---|---|
| RT | RRT | Area | Area % | RT | RRT | Area | Area % |
|  |  |  |  | 1.85 | 0.21 | 1.60 | 0.02 |
| 4.16 | 0.48 | 2.84 | 0.02 | 4.16 | 0.48 | 2.71 | 0.02 |
| 8.71 | 1.00 | 13314.70 | 99.98 | 8.71 | 1.00 | 13570.50 | 99.96 |

Incubated for 1 Month at 40 or 50° C.

| 40° C. | | | | 50° C. | | | |
|---|---|---|---|---|---|---|---|
| RT | RRT | Area | Area % | RT | RRT | Area | Area % |
| 3.62 | 0.48 | 2.46 | 0.02 | 3.62 | 0.48 | 2.53 | 0.02 |
| 7.59 | 1.00 | 11839.00 | 99.98 | 7.59 | 1.00 | 11870.80 | 99.98 |

As can be seen from the results set forth in Table 5, there was no detectable chemical degradation for this formulation under these conditions.

The chemical stability of IBU formulations at 4, 8, and 16 mg/mL containing $Na_3PO_4$ with a molar ratio of 0.8:1.0 ($Na_3PO_4$:IBU) was determined after autoclaving samples in glass vials. The results are set forth in Table 6 below.

TABLE 6

Chemical stability, content, and pH of 4, 8, and 16 mg/mL IBU formulations containing $Na_3PO_4$

| | Before Filtering | | | | After Filtering | | | | After Autoclaving | | | |
|---|---|---|---|---|---|---|---|---|---|---|---|---|
| | RT | RRT | Area | Area % | RT | RRT | Area | Area % | RT | RRT | Area | Area % |
| | 4 mg/mL, IBU:Na$_3$PO$_4$ (1.0:0.8) | | | | | | | | | | | |
| | 4.17 | 0.48 | 2.04 | 0.02 | 4.16 | 0.48 | 1.97 | 0.02 | 4.14 | 0.48 | 2.45 | 0.02 |
| | 8.73 | 1.00 | 10725.00 | 99.98 | 8.73 | 1.00 | 10587.20 | 99.98 | 8.67 | 1.00 | 10600.10 | 99.98 |
| | 4 mg/mL, IBU:Na$_3$PO$_4$ (1.0:0.8) | | | | | | | | | | | |
| Content (mg/mL) | 3.99 | | | | 3.94 | | | | 3.94 | | | |
| pH | 7.62 | | | | 7.58 | | | | 7.62 | | | |
| | 8 mg/mL, IBU:Na$_3$PO$_4$ (1.0:0.8) | | | | | | | | | | | |
| | 4.17 | 0.48 | 2.19 | 0.02 | 4.16 | 0.48 | 2.22 | 0.02 | 4.13 | 0.48 | 2.23 | 0.02 |
| | 8.74 | 1.00 | 10905.00 | 99.98 | 8.71 | 1.00 | 10714.30 | 99.98 | 8.67 | 1.00 | 10655.80 | 99.98 |
| | 8 mg/mL, IBU:Na$_3$PO$_4$ (1.0:0.8) | | | | | | | | | | | |
| Content (mg/mL) | 8.12 | | | | 7.97 | | | | 7.93 | | | |
| pH | 7.43 | | | | 7.54 | | | | 7.53 | | | |
| | 16 mg/mL, IBU:Na$_3$PO$_4$ (1.0:0.8) | | | | | | | | | | | |
| | 4.16 | 0.48 | 2.05 | 0.02 | 4.14 | 0.48 | 2.15 | 0.02 | 4.14 | 0.48 | 2.18 | 0.02 |
| | 8.72 | 1.00 | 10540.80 | 99.98 | 8.69 | 1.00 | 10503.60 | 99.98 | 8.67 | 1.00 | 10970.60 | 99.98 |
| | 16 mg/mL, IBU:Na3Pa4 (1.0:0.8) | | | | | | | | | | | |
| Content (mg/mL) | 15.69 | | | | 16.33 | | | | 15.63 | | | |
| pH | 7.47 | | | | 7.47 | | | | 7.49 | | | |

As can be seen from the results set forth in Table 6, there was no detectable chemical degradation for these formulations under these conditions.

Example 6

Solubility of Ibuprofen: Sodium Hydroxide Formulations

Ibuprofen was soluble up to 100 mg/mL with Sodium Hydroxide (NaOH) at molar ratios of 0.95:1.0, 1.0:1.0, and 1.05:1.0 (NaOH:IBU). Upon sample dilution the solution became a cloudy white precipitate at molar ratios of 0.95:1.0 and 1.0:1.0 (Table 7). When the IBU sample at the 1.05:1.0 (NaOH:IBU) molar ratio was diluted to lower concentrations, the solution was clear and colorless at each concentration (Table 2).

TABLE 7

Solubility of IBU with NaOH

| | NaOH:IBU | | | | | |
|---|---|---|---|---|---|---|
| Molar Ratio | 0.95:1.00 | | 1.00:1.00 | | 1.05:1.00 | |
| Concentration (mg/mL) | Appearance | pH | Appearance | pH | Appearance | pH |
| 100 | Clear, colorless | 7.35 | Clear, colorless | 7.61 | Clear, colorless | 10.09 |
| 25 | Clear, colorless | 7.05 | Cloudy White ppt | 7.09 | Clear, colorless | 9.81 |
| 10 | Cloudy white haze | 6.73 | Cloudy White ppt | 6.77 | Clear, colorless | 9.75 |
| 8 | Cloudy white haze | 6.71 | Chunky White ppt | 6.70 | Clear, colorless | 9.71 |
| 4 | white haze | 6.44 | White ppt | 6.48 | Clear, colorless | 9.53 |
| 3.2 | white haze | 6.35 | White ppt | 6.34 | Clear, colorless | 9.43 |

Example 6

Solubility of Ibuprofen: L-Lysine Formulations

Ibuprofen solutions were made at concentrations of 3.2, 4.0, and 8.0 mg/mL with L-Lysine (Lys) base. Ibuprofen was able to be dissolved at these concentrations only at a molar ratio of ~1.0:1.0 (Lys:IBU) (Table 8).

TABLE 8

Solubility of IBU with Lys.
IBU dissolved with L-Lysine

| IBU Conc. (mg/mL) | Lys:IBU Final Molar Ratio | Appearance | pH |
|---|---|---|---|
| 3.2 | 1.019:1.000 | Clear and colorless | 6.83 |
| 4.0 | 1.003:1.000 | Clear and colorless | 6.84 |
| 8.0 | 0.995:1.000 | Clear and colorless | 6.83 |

Example 6

Solubility of Ibuprofen with Sodium and Potassium Carbonate

Ibuprofen was dissolved at 100 mg/mL with both potassium and sodium carbonate at molar ratios ranging from 0.5:1.0 to 0.9:1.0 ($Na_2CO_3$/$K_2CO_3$:IBU). The solutions were clear and colorless at all concentrations tested when the molar ratio was 0.6:1.0 to 0.9:1.0 using either $Na_2CO_3$ (Table 9) or $K_2CO_3$ (Table 10).

TABLE 9

Solubility of IBU with $Na_2CO_3$

| | $Na_2CO_3$:IBU | | | | | | | | | |
|---|---|---|---|---|---|---|---|---|---|---|
| Molar Ratio | 0.5:1.0 | | 0.6:1.0 | | 0.7:1.0 | | 0.8:1.0 | | 0.9:1.0 | |
| Concentration (mg/mL) | Appearance | pH | Appearance | pH | Appearance | pH | Appearance | pH | Appearance | pH |
| 100 | Clear, colorless | 7.56 | Clear, colorless | 7.50 | Clear, colorless | 7.69 | Clear, colorless | 8.01 | Clear, colorless | 8.11 |
| 25 | White ppt | 7.14 | Clear, colorless | 7.72 | Clear, colorless | 8.29 | Clear, colorless | 8.45 | Clear, colorless | 8.54 |
| 10 | White Chunky ppt | 6.90 | Clear, colorless | 7.93 | Clear, colorless | 8.46 | Clear, colorless | 8.59 | Clear, colorless | 8.69 |
| 8 | White Chunky ppt | 6.76 | Clear, colorless | 8.00 | Clear, colorless | 8.51 | Clear, colorless | 8.62 | Clear, colorless | 8.72 |
| 4 | White ppt | 6.56 | Clear, colorless | 8.05 | Clear, colorless | 8.57 | Clear, colorless | 8.69 | Clear, colorless | 8.79 |
| 3.2 | Very Slight white ppt | 6.50 | Clear, colorless | 8.09 | Clear, colorless | 8.58 | Clear, colorless | 8.71 | Clear, colorless | 8.81 |

TABLE 10

Solubility of IBU with $K_2CO_3$.

| | $K_2CO_3$:IBU | | | | | | | | | | | |
|---|---|---|---|---|---|---|---|---|---|---|---|---|
| Molar Ratio | 0.5:1.0 | | 0.6:1.0 | | 0.7:1.0 | | 0.8:1.0 | | 0.9:1.0 | | 1.0:1.0 | |
| Concentration (mg/mL) | Appearance | pH | Appearance | pH | Appearance | pH | Appearance | pH | Appearance | pH | Appearance | pH |
| 100 | Clear, colorless | 7.37 | Clear, colorless | 7.49 | Clear, colorless | 7.43 | Clear, colorless | 7.74 | Clear, colorless | 8.23 | Clear, colorless | 8.57 |
| 25 | White haze, ppt | 6.90 | Clear, colorless | 8.02 | Clear, colorless | 8.18 | Clear, colorless | 8.28 | Clear, colorless | 8.45 | Clear, colorless | 8.79 |

TABLE 10-continued

Solubility of IBU with $K_2CO_3$.

| | $K_2CO_3$:IBU | | | | | | | | | | | |
|---|---|---|---|---|---|---|---|---|---|---|---|---|
| Molar Ratio | 0.5:1.0 | | 0.6:1.0 | | 0.7:1.0 | | 0.8:1.0 | | 0.9:1.0 | | 1.0:1.0 | |
| Concentration (mg/mL) | Appearance | pH | Appearance | pH | Appearance | pH | Appearance | pH | Appearance | pH | Appearance | pH |
| 10 | White haze, ppt | 6.80 | Clear, colorless | 8.15 | Clear, colorless | 8.29 | Clear, colorless | 8.50 | Clear, colorless | 8.57 | Clear, colorless | 8.90 |
| 8 | White haze, ppt | 6.78 | Clear, colorless | 8.18 | Clear, colorless | 8.32 | Clear, colorless | 8.52 | Clear, colorless | 8.60 | Clear, colorless | 8.92 |
| 4 | White haze | 6.56 | Clear, colorless | 8.24 | Clear, colorless | 8.39 | Clear, colorless | 8.58 | Clear, colorless | 8.67 | Clear, colorless | 8.98 |
| 3.2 | White haze | 6.44 | Clear, colorless | 8.25 | Clear, colorless | 8.40 | Clear, colorless | 8.59 | Clear, colorless | 8.68 | Clear, colorless | 9.00 |

While $Na_2CO_3$ displayed useful properties as a solubilizer for ibuprofen, a 10 mg/mL IBU formulation with $Na_2CO_3$ became hazy and displayed undesirable pH shifts during stability testing.

Comparative Example A

In Comparative Example A, Megulmine was used as a solubilizer for ibuprofen. Ibuprofen was soluble with Meglumine (Meg) at 100 mg/mL when made at a molar ratio of 0.9:1.0 (Meg:IBU). When the sample was diluted to lower concentrations the clear and colorless solution became hazy and then formed a cloudy white precipitate (Table 11).

TABLE 11

Solubility of IBU with Meg

| Concentration | Meg:IBU (Molar Ratio, 0.90:1.00) | |
|---|---|---|
| (mg/mL) | Appearance | pH |
| 100 | Clear and colorless | 7.19 |
| 25 | White Haze | 6.62 |
| 10 | Cloudy white ppt | 6.67 |
| 8 | Cloudy white ppt | 6.63 |
| 4 | Cloudy White ppt | 6.38 |
| 3.2 | Cloudy White ppt | 6.30 |

Comparative Examples B-E

In Comparative Examples B-E, other potential ibuprofen solubilizing agents were utilized to form aqueous solutions of ibuprofen at a molar ratio of solubilizing agent to ibuprofen of 0.90 to 1.0. In Comparative Example B, sodium bicarbonate was used as the ibuprofen solubilizing agent. In Comparative Example C, sodium citrate dihydrate was used. In Comparative Example D, dibasic potassium phosphate was used as the ibuprofen solubilizing agent. Sodium bicarbonate, sodium citrate dihydrate, and dibasic potassium phosphate were unable to dissolve Ibuprofen at 100 mg/mL using a molar ratio of 0.9 to 1.0 of base/buffer to IBU. In Comparative Example E, trisodium citrate was used as the ibuprofen solubilizing agent. Trisodium citrate was unable to dissolve Ibuprofen at 50 mg/mL IBU with 0.9:1.0 Trisodium Citrate:IBU. The sample contained a significant amount of precipitate which remained even when the ratio was increased to 1:1.

Comparative Example F

In Comparative Example F, diethanolamine was utilized as a ibuprofen solubilizing agent to form aqueous solutions of ibuprofen. The ibuprofen was solubilized at 100 mg/mL at a molar ratio of ibuprofen solubilizing agent to ibuprofen of 0.95 to 1.0 (pH=7.00). Thereafter, the ibuprofen diluted. The results are provided in Table 12 below:

TABLE 12

| Dilution (mg/mL) | Appearance | pH |
|---|---|---|
| 25 | Cloudy white haze | 6.72 |
| 10 | Bright White ppt | 6.23 |
| 8 | Cloudy white ppt | 6.68 |
| 4 | Cloudy white ppt | 6.39 |
| 3.2 | Cloudy White ppt | 6.30 |

Triethanolamine was able to solubilize ibuprofen at a molar ratio of approximately 1:1 but when diluted it also precipitated like diethanolamine. It is hypothesized that monoethanolamine may behave similarly.

Example 7

The objective of Example 7 was to assess the acute irritation potential of aqueous solutions of ibuprofen using sodium phosphate and potassium phosphate as ibuprofen solubilizing agents when injected intravenously into rabbits.

The test articles for this study were as follows:

Test Article 1: Caldolor® (Ibuprofen) Injection

Test Article 2: Ibuprofen (5 mg/mL) in $Na_3PO_4$

Test Article 3: Ibuprofen (10 mg/mL) in $Na_3PO_4$

Test Article 4: Ibuprofen (80 mg/mL) in $Na_3PO_4$

Test Article 5: Ibuprofen (10 mg/mL) in $K_3PO_4$.

Rabbits were divided into in Groups 1-6, and were dosed once by slow bolus intravenous injection over approximately 60 seconds into the ear vein. Animals were dosed at concentrations of 1 mL/kg (Vehicle), 4 mg/mL (Test Article 1), 5 mg/mL (Test Article 2), 10 mg/mL (Test Articles 3 and 5), and 80 mg/mL (Test Article 4). The molar ratio of $Na_3PO_4$ and $K_3PO_4$ to ibuprofen in this study was 0.9:1 and also contained sodium chloride to make an iso-osmotic solution. Animals were euthanized by intravenous barbiturate overdose following the final skin/dermal grading.

Table 13 below reflects the study design as it pertained to the pathology aspect of this study.

TABLE 13

| Group | Number/Group | Dose Concentration Left Ear* | Dose Concentration Right Ear* | Sacrifice Time (hr) |
|---|---|---|---|---|
| 1 | 3 | 4 mg/mL Test Article 1 | 5 mg/mL Test Article 2 | 1 |
| 2 | 3 | 4 mg/mL Test Article 1 | 5 mg/mL Test Article 2 | 24 |
| 3 | 3 | 10 mg/mL Test Article 5 | 10 mg/mL Test Article 3 | 1 |
| 4 | 3 | 10 mg/mL Test Article 5 | 10 mg/mL Test Article 3 | 24 |
| 5 | 3 | 80 mg/mL Test Article 4 | 1 mL/kg Vehicle | 1 |
| 6 | 3 | 80 mg/mL Test Article 4 | 1 mL/kg Vehicle | 24 |

*Dose Volume 1 mL/kg administered over approximately 60 seconds.

No gross necropsy was performed at in-life termination. After the animals were euthanized, a full thickness section (approximately 6×6 cm) of the pinna of both ears, including the artery and the site of injection, were excised and fixed in 10% neutral buffered formalin for histopathological evaluation.

Table 14 below provides draize scoring with erythema and edema scores at 1 hour post injection (Groups 1, 3 and 5) and at 1 and 24 hours post injection (Groups 2 and 4).

TABLE 14

Injection site scoring (Draize)

1 hour

| Group 1 | | | Left 4 mg/mL Test Article 1 | | Right 5 mg/mL Test Article 2 | |
|---|---|---|---|---|---|---|
| Animal # | Sex | Group | ER | ED | ER | ED |
| 601 | M | 1 | 2 | 1 | 1 | 0 |
| 602 | M | 1 | 2 | 2 | 1 | 0 |
| 603 | F | 1 | 1 | 0 | 1 | 0 |

| | | | 1 hour | | | | 24 hour | | | |
|---|---|---|---|---|---|---|---|---|---|---|
| Group 2 | | | Left 4 mg/mL Test Article 1 | | Right 5 mg/mL Test Article 2 | | Left 4 mg/mL Test Article 1 | | Right 5 mg/mL Test Article 2 | |
| Animal # | Sex | Group | ER | ED | ER | ED | ER | ED | ER | ED |
| 604 | M | 2 | 0 | 0 | 0 | 0 | 0 | 0 | 0 | 0 |
| 605 | F | 2 | 1 | 1 | 1 | 1 | 0 | 0 | 0 | 0 |
| 606 | F | 2 | 1 | 1 | 1 | 1 | 1 | 0 | 1 | 0 |

1 hour

| Group 3 | | | Left 10 mg/mL Test Article 5 | | Right 10 mg/mL Test Article 3 | |
|---|---|---|---|---|---|---|
| Animal # | Sex | Group | ER | ED | ER | ED |
| 607 | M | 3 | 2 | 1 | 2 | 1 |
| 608 | M | 3 | 0 | 0 | 0 | 0 |
| 609 | F | 3 | 1 | 0 | 1 | 0 |

| | | | 1 hour | | | | 24 hour | | | |
|---|---|---|---|---|---|---|---|---|---|---|
| Group 4 | | | Left 10 mg/mL Test Article 5 | | Right 10 mg/mL Test Article 3 | | Left 10 mg/mL Test Article 5 | | Right 10 mg/mL Test Article 3 | |
| Animal # | Sex | Group | ER | ED | ER | ED | ER | ED | ER | ED |
| 610 | M | 4 | 1 | 0 | 1 | 0 | 3 | 2 | 1 | 1 |
| 611 | F | 4 | 0 | 0 | 0 | 0 | 3 | 1 | 2 | 0 |
| 612 | F | 4 | 1 | 0 | 0 | 0 | 2 | 1 | 0 | 0 |

1 hour

| Group 5 | | | Left 80 mg/mL Test Article 4 | | Right 1 mL/mL Vehicle | |
|---|---|---|---|---|---|---|
| Animal # | Sex | Group | ER | ED | ER | ED |
| 613 | M | 5 | 3 | 3 | 0 | 0 |
| 614 | M | 5 | 2 | 2 | 0 | 0 |
| 615 | F | 5 | 3 | 3 | 0 | 0 |

TABLE 14-continued

| | | | Injection site scoring (Draize) | | | | | | |
|---|---|---|---|---|---|---|---|---|---|
| | | | 1 hour | | | | 24 hour | | |
| | | | Left 80 mg/mL Test Article 4 | | Right 1 mL/mL Vehicle | | Left 80 mg/mL Test Article 4 | | Right 1 mL/mL Vehicle | |
| Group 6 | | | | | | | | | | |
| Animal # | Sex | Group | ER | ED | ER | ED | ER | ED | ER | ED |
| 616 | M | 6 | 2 | 1 | 0 | 0 | 4 | 4 | 1 | 0 |
| 617 | F | 6 | 3 | 2 | 0 | 0 | 4 | 4 | 0 | 0 |
| 618 | F | 6 | 3 | 2 | 0 | 0 | 4 | 4 | 0 | 0 |

R
ER = Erythema
ED = Edema

Injection with Vehicle (Groups 5 and 6, right ear)
At one hour, animals injected with the vehicle exhibited hemorrhage, vascular necrosis and edema. At 24 hours, animals injected with the vehicle were essentially normal, with only one animal exhibiting moderate edema. Lesions at one hour are associated with the mechanical aspect of injection.

Test Article 1—Caldolor® (Ibuprofen) Injection (Groups 1 and 2, left ear)
At one hour, only one animal exhibited microscopic change, that being vascular necrosis and hemorrhage. At 24 hours, all animals were microscopically normal, indicating that the change at one hour was most likely associated with the mechanical aspect of injection.

Test Article 2: Ibuprofen (5 mg/mL) in $Na_3PO_4$ (Groups 1 and 2, right ear)
At one hour, all animals exhibited edema. One also exhibited minimal vascular necrosis, while a second had a minimal mixed cell inflammation composed of 100% mononuclear cells. At 24 hours, two of three animals only exhibited slight to minimal hemorrhage, while the third had moderate vascular necrosis with mild hemorrhage and a minimal inflammatory response composed of 80% neutrophils.

Test Article 3: Ibuprofen (10 mg/mL) in $Na_3PO_4$ (Groups 3 and 4, right ear)
At one hour, only one animal exhibited a microscopic change, that being mild edema. At 24 hours, one animal exhibited mild edema and a second animal exhibited mild hemorrhage.

Test Article 4: Ibuprofen (80 mg/mL) in $Na_3PO_4$ (Groups 5 and 6, left ear)
At one hour, one animal exhibited mild edema, mild vascular necrosis and mild hemorrhage. At 24 hours, all three animals exhibited mild vascular necrosis with mild to moderate inflammation, comprised of 90 or 100% neutrophils. Moderate hemorrhage was noted in all animals.

Test Article 5: Ibuprofen (10 mg/mL) in $K_3PO_4$ (Groups 3 and 4, left ear)
At one hour, two animals exhibited mild to moderate vascular necrosis with a corresponding mild to moderate hemorrhage. The third animal of the group exhibited mild edema. At 24 hours, one animal was normal, one exhibited only minimal vascular necrosis, while the third had mild edema, mild vascular necrosis, mild hemorrhage and a minimal inflammatory infiltrate comprised of 80% neutrophils.

SUMMARY OF RESULTS

The results from Table 14 show that the current commercially available product (Caldolor®) diluted to 4 mg/mL (as is done when the product is infused into patients) is similar to the sodium phosphate ($Na_3PO_4$) 5 mg/mL and 10 mg/mL formulations at 1 and 24 hours. The potassium phosphate ($K_3PO_4$) formulation at 10 mg/mL (test article 5) showed a greater amount of erythema at 24 hours. The undiluted sodium phosphate formulation at 80 mg/mL showed more erythema and edema at 1 and 24 hours. The current formulation (Caldolor®) at 4 mg/mL, the 5 mg/mL and 10 mg/mL sodium phosphate and vehicle all provided similar results. The potassium phosphate formulation at 10 mg/mL was somewhat more irritating. The undiluted 80 mg/mL sodium phosphate formulation the most irritating.

CONCLUSION

It will be readily apparent to one of ordinary skill in the relevant arts that other suitable modifications and adaptations to the methods and applications described herein are suitable and may be made without departing from the scope of the invention or any embodiment thereof. While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims.

We claim:
1. A pre-filled bag for intravenous injection containing a stable pharmaceutical composition comprising water for injection, 4 mg/mL ibuprofen, sodium chloride, and sodium hydroxide, wherein the sodium hydroxide to ibuprofen molar ratio is at least 1.05:1, and wherein the pharmaceutical composition is clear and has a pH of 7.4.

2. The pre-filled bag according to claim 1, wherein the bag is made of a material selected from the group consisting of polypropylene, polyolefin, and polyvinylchloride.

3. The pre-filled bag according to claim 2, wherein the material is polypropylene.

4. The pre-filled bag according to claim 1, wherein the pharmaceutical composition is sterile filtered or terminally sterilized.

5. The pre-filled bag according to claim 1, wherein the pharmaceutical composition remains clear when exposed to at least one freeze-thaw cycle.

6. The pre-filled bag according to claim 1, wherein the pharmaceutical composition is clear when stored for at least 12 weeks at ambient temperature.

7. The pre-filled bag according to claim 1, wherein the pharmaceutical composition shows no detectable chemical degradation after incubation for one month at 40° C.

8. A pre-filled bag for intravenous injection containing a stable pharmaceutical composition comprising water for injection, 800 mg ibuprofen, sodium chloride, and sodium hydroxide, wherein the sodium hydroxide to ibuprofen molar ratio is at least 1.05:1, and wherein the pharmaceutical composition is clear and has a pH of 7.4.

9. The pre-filled bag according to claim 8, wherein the bag is made of a material selected from the group consisting of polypropylene, polyolefin, and polyvinylchloride.

10. The pre-filled bag according to claim 9, wherein the material is polypropylene.

11. The pre-filled bag according to claim 8, wherein the pharmaceutical composition is sterile filtered or terminally sterilized.

12. The pre-filled bag according to claim 8, wherein the pharmaceutical composition remains clear when exposed to at least one freeze-thaw cycle.

13. The pre-filled bag according to claim 8, wherein the pharmaceutical composition is clear when stored for at least 12 weeks at ambient temperature.

14. The pre-filled bag according to claim 8, wherein the pharmaceutical composition shows no detectable chemical degradation after incubation for one month at 40° C.

15. A method of treating pain in a patient, comprising administering the pharmaceutical composition from the pre-filled bag according to claim 1 intravenously to the patient.

16. A method of treating fever in a patient, comprising administering the pharmaceutical composition from the pre-filled bag according to claim 1 intravenously to the patient.

* * * * *